United States Patent [19]

Raisanen

[11] Patent Number: 5,759,493
[45] Date of Patent: Jun. 2, 1998

[54] APPARATUS FOR DETECTING A SPECIFIED GAS WITHIN A MIXTURE

[75] Inventor: Walfred R. Raisanen, Paradise Valley, Ariz.

[73] Assignee: Arizona Instrument Corporation, Phoenix, Ariz.

[21] Appl. No.: 640,162

[22] Filed: Apr. 30, 1996

[51] Int. Cl.$^6$ ................................................. G01N 27/00
[52] U.S. Cl. ........................... 422/98; 422/83; 422/98; 422/90
[58] Field of Search ................. 73/31.01, 31.02; 422/83, 88, 90, 98, 93; 430/311, 315, 316, 317

[56] References Cited

U.S. PATENT DOCUMENTS

| | | | |
|---|---|---|---|
| 3,578,409 | 5/1971 | Silverman | 23/254 |
| 3,714,562 | 1/1973 | McNerney | 324/65 |
| 4,343,768 | 8/1982 | Kimura | 422/97 |
| 4,478,076 | 10/1984 | Bohrer | 73/204 |
| 4,478,077 | 10/1984 | Bohrer et al. | 73/204 |
| 4,952,904 | 8/1990 | Johnson et al. | 338/36 |
| 5,010,021 | 4/1991 | Bell et al. | 436/120 |
| 5,087,574 | 2/1992 | Bell et al. | 436/120 |
| 5,145,645 | 9/1992 | Zakin et al. | 422/98 |
| 5,345,213 | 9/1994 | Semancik et al. | 338/34 |
| 5,356,756 | 10/1994 | Cavicchi et al. | 430/315 |

OTHER PUBLICATIONS

Read et al. "Mechanical Behavior of Aluminum and Copper Thin Films" Mechanics and Materials for Electronic Packaging American Society of Mechanical Engineers, Applied Mechanics Division. AMD vol. 187(1994). ASME, New York, NY, USA, pp. 41–49. Abstract Only.

*Primary Examiner*—Jeffrey Stucker
*Attorney, Agent, or Firm*—Meschkow & Gresham, P.L.C.; Jordan M. Meschkow; Lowell W. Gresham

[57] ABSTRACT

A gas sensor for detecting the presence of a specified gas within a mixture includes a silicon substrate, a silicon nitride membrane supported by the substrate, a thin gold sensor trace deposited on the membrane, and a thin gold reference trace deposited on the membrane. A molybdenum adhesion layer is employed between the membrane and the gold traces. The electrical resistance of the sensor trace changes when the sensor trace adsorbs molecules of the gas. Solid state construction facilitates quick and efficient regeneration of the sensing capability of the gas sensor. The silicon nitride membrane and the molybdenum adhesion layer do not adversely affect the resistivity of the gold traces. An alternate gas sensor embodiment includes an integrally formed heater element.

35 Claims, 4 Drawing Sheets

APPARATUS FOR DETECTING A SPECIFIED GAS WITHIN A MIXTURE

BACKGROUND OF THE INVENTION

1. Field of the Invention

The present invention relates generally to electronic sensors for detecting the presence of certain gases in a gaseous mixture. In particular, the present invention relates to gas sensors that detect changes in the resistivity of thin film sensing elements caused by adsorption of gas molecules by the sensing elements.

2. The Prior Art

Instruments for detecting the presence of certain gases within a gaseous mixture are generally known. Such instruments are typically utilized where specific vapors, e.g., mercury vapor or sulfur dioxide, may be produced or otherwise released into the environment. Gas sensors often rely upon reactions that occur between the detected gas and reactive sensor elements. For example, one known gas sensor incorporates a heating element designed to contact and burn a quantity of the gas under observation. The combustion of the gas alters a measurable electrical characteristic (e.g., resistance) of the heating element. Changes in this electrical characteristic indicate the presence of the gas.

Other gas sensors utilize the principle of adsorption to detect the presence of certain gases. One known sensor includes a thin layer of gold deposited on a ceramic substrate. The resistance of the gold layer changes when molecules of the gas are adsorbed by the gold layer. Ceramic-based sensors are large and bulky in comparison to miniature solid state sensors. Consequently, conventional adsorptive gas sensors are inefficient to operate and expensive to manufacture.

Adsorptive gas sensors are typically regenerated after adsorbing a sufficient amount of the gas to trigger an indication circuit. Regeneration of a gold sensor layer involves heating the gold to liberate the gas molecules that have migrated into the grain boundaries of the gold layer. Depending upon the type of gas adsorbed by the gold layer, regeneration temperatures can exceed 250° C. Due to the low thermal resistivity of ceramic substrates, a ceramic "macro" sensor requires a large amount of power (30–60 Watts) to heat the gold layer for regeneration. Consequently, ceramic gas sensors are often limited to use in areas where 120 VAC or suitable power generators are available.

In addition to the high regeneration power associated with large ceramic sensors, the speed of regeneration is undesirably slow. A ceramic macro sensor may require 10–30 minutes of heating time to regenerate the sensing capacity of the gold layer. As such, ceramic gas sensors cannot be used for real time monitoring of gases without implementing isolated back-up sensors, overlapping regeneration cycles, or other devices and/or processes that can affect the reliability and increase the cost of the gas detection equipment.

Some prior art gas sensors utilize external heating elements to heat the gold layers to the regeneration temperature. Unfortunately, such external heating elements may be difficult to manufacture and calibrate for specific sensor applications. Furthermore, the amount of heat generated by such heating elements may vary over the surface of the sensing layer. Uneven heating is undesirable because it can cause insufficient or inconsistent regeneration.

Ceramic gas sensors can be relatively expensive because they are not mass produced in large batch quantities. In addition, the electrical and physical characteristics of the sensors may vary on an individual basis. Increased calibration efforts may be required to compensate for variations in electrical characteristics such as the resistivity of the gold sensor layer. Consistency in such characteristics is especially important where a reference sensor element is combined with an active sensor element to provide a relative indication of the change in an electrical parameter.

Materials commonly used to manufacture solid state sensors may be undesirable for adsorptive gold gas sensors. For example, silicon dioxide, which is often used as a support membrane for sensor films, tends to alter the resistivity of gold sensor films. Uncontrolled changes in the sensor film electrical characteristics can cause calibration problems or inaccurate measurements. As another example, chromium is commonly used as an adhesion layer between support membranes and metallic film elements. Unfortunately, chromium tends to migrate into (and alter the resistivity of) thin gold films. As such, solid state adsorptive gold sensors have not been adequately developed in the past.

SUMMARY OF THE INVENTION

Accordingly, it is an advantage of the present invention that an improved sensor for detecting the presence of a specified gas within a mixture is provided.

Another advantage of the present invention is that the power required to regenerate the sensor is substantially lower than the power required to regenerate an equivalent ceramic substrate sensor.

Another advantage is that the regeneration time associated with the sensor is substantially shorter than the regeneration time associated with an equivalent ceramic substrate sensor.

A further advantage is that the short regeneration time associated with the sensor enables approximately real time monitoring for the presence of the specified gas.

Another advantage is that the present invention provides a gas sensor having an integral heating element capable of evenly heating the gas sensor during regeneration.

Another advantage of the present invention is that solid state manufacturing techniques can be utilized to batch produce many individual sensors having consistent physical and electrical characteristics.

A further advantage is that batch production of the sensors reduces manufacturing and calibration costs.

Another advantage is that the sensor includes a gold film sensor element having electrical characteristics that are not adversely affected by the supporting substrate material or the adhesion layer material.

The above and other advantages of the present invention are carried out in one form by an apparatus for detecting the presence of a specified gas within a mixture. The apparatus includes a substrate, a silicon nitride membrane supported by the substrate, a low-mobility adhesion layer, e.g., molybdenum deposited on the membrane, and a gold sensor trace deposited on the adhesion layer. The sensor trace is capable of adsorbing molecules of the specified gas.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENT

Figure 1:
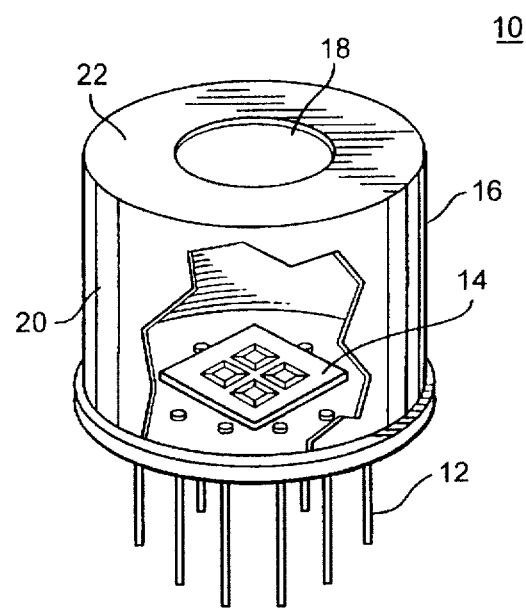
FIG. 1 is a cut-away perspective view of a gas sensor according to the present invention.

FIG. 1 shows a cut-away perspective view of a gas sensor 10 according to the preferred embodiment of the present invention. Gas sensor 10 is configured to detect the presence of a specified gas (such as mercury vapor or hydrogen sulfide vapor) within a mixture (such as air). For purposes of the following description, the "specified gas" is mercury or hydrogen sulfide vapor and the "mixture" is air. Of course, the present invention is not limited to the detection of mercury or hydrogen sulfide vapor or the analysis of air samples. Those skilled in the art will appreciate that it is possible to modify gas sensor 10 such that other gases or compounds may be monitored.

Gas sensor 10 can be electrically connected to conventional gas detection equipment (not shown) via conductor pins 12. For example, gas sensor 10 may couple to conventional power, control, and processing circuits (not shown) as necessary for the particular application. Gas sensor 10 generally includes a sensor chip 14 mounted within a container 16 configured to accommodate it. Sensor chip 14 preferably detects the presence of mercury or hydrogen sulfide vapor in an air sample which flows past gas sensor 10. In accordance with known methodologies, the air sample may be passed through pumps, filters, valves, and other components (not shown) before reaching gas sensor 10.

In the preferred embodiment, an inlet hole 18 formed within container 16 allows air to be introduced into container 16. Container 16 includes a cylindrically shaped wall 20 and a top cover 22 integrally formed with wall 20. Inlet hole 18 is formed in top cover 22 and is sized to regulate the flow of air into container 16. The size of inlet hole 18 regulates the flow of air by allowing the air to enter container 16, pass over sensor chip 14, and exit container 16 via eddy currents generated inside of container 16. In practice, an amount of air enters container 16 near the center of inlet hole 18 while an amount of air concurrently exits container 16 near the perimeter of inlet hole 18.

In one exemplary embodiment, inlet hole 18 is approximately 0.12 inches in diameter and air flows into container 16 at a rate between 50 and 500 ml/min. The precise size of inlet hole 18 may be dependent upon the sensitivity of sensor chip 14, the flow rate of the air sample past gas sensor 10, and other application-specific parameters.

With reference to FIGS. 2–5, various views of sensor chip 14 are illustrated in detail. Sensor chip 14 generally includes a silicon substrate 24, a silicon nitride membrane 26 supported by substrate 24, and a number of cavities 28 formed within substrate 24. Cavities 28 are formed under membrane 26 such that membrane 26 forms a number of platforms 30 suspended above cavities 28 (see FIG. 2). In the preferred embodiment, a thin gold sensor trace 32 and a thin gold reference trace 34 are located on each platform 30. Nothing limits the present invention to the four "microsensor" configuration shown and described herein, and more or less microsensor elements having any number of sensor traces 32 and/or reference elements 34 may be utilized to meet specific application requirements.

Sensor chip 14 is approximately 0.10 inches square, and is batch-produced in accordance with known solid state manufacturing techniques. Substrate 24 is formed from silicon having a crystal orientation of |1.0.0|. This preferred crystal orientation facilitates directional etching during the manufacturing process described below. Silicon nitride is deposited on substrate 24 to form membrane 26 having a preferred thickness of 10.000 Angstroms. A number of apertures 36 (shown in FIG. 2 as trapezoidal regions surrounding platforms 30) are patterned and etched through membrane 26 to expose the underlying silicon substrate 24.

Figure 3:
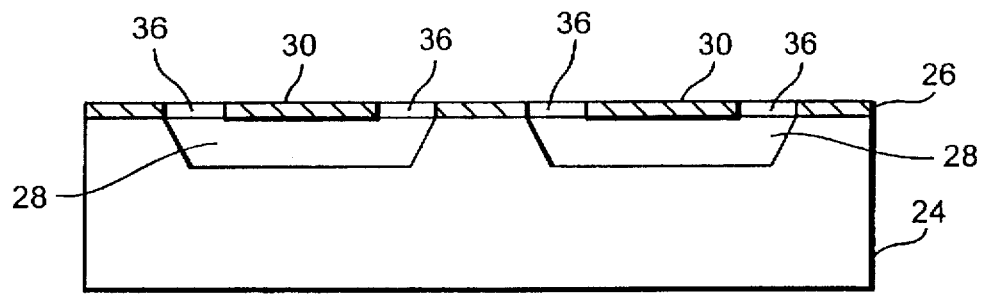
FIG. 3 is a side sectional view of the sensor chip as viewed from line 3—3 in FIG. 1.

Cavities 28 are formed under platforms 30 by directionally etching silicon substrate 24 to an appropriate depth. FIG. 3 shows cavities 28 formed within substrate 24 (for clarity, sensor traces 32 and reference elements 34 are not included in FIG. 3). Silicon etching processes are known to those skilled in the art and such processes will not be described in detail herein. The etching process attacks silicon substrate 24 while leaving silicon nitride membrane 26 substantially intact. Following the silicon etching process, platforms 30 are left suspended over cavities 28. The portions of membrane 26 that form platforms 30 are supported by substrate 24 via a number of support legs 38.

In the preferred embodiment, sensor traces 32 and reference elements 34 are formed from a thin layer of electrically conductive gold. Gold sensor traces 32 are desirable for the detection of mercury and hydrogen sulfide vapors because gold is capable of adsorbing molecules of such gases. The adsorption of foreign molecules alters the electrical resistivity of sensor traces 32. As such, the silicon nitride composition of membrane 26 is desirable because silicon nitride does not affect the resistivity of thin gold traces. Those familiar with microsensor technology will recognize that silicon dioxide (a material commonly used in such applications) would be unsuitable for membrane 26 because it can alter the resistivity of thin gold traces.

An adhesion layer 40 (see FIG. 5) is used to facilitate the adhesion of sensor traces 32 and reference traces 34 to membrane 30. Adhesion layer 40 is formed from a material having a relatively low mobility relative to sensor traces 32 and reference traces 34. For purposes of this description, a "low-mobility" material has a relatively low diffusion constant with respect to the material used for sensor and reference traces 32 and 34. In the preferred embodiment, molybdenum is deposited on membrane 30 using conventional evaporation techniques. Molybdenum is utilized for adhesion layer 40 because it does not migrate into (and affect the resistivity of) gold. In contrast, chromium, which is commonly used as an adhesion layer, tends to adversely affect the resistive characteristics of thin gold sensors. Adhesion layer 40 may alternatively be formed from titanium, tungsten, titanium-tungsten alloy, or other suitable low-mobility metals.

The thin gold sensor traces 32 and gold reference elements 34 are deposited on the upper surface of platforms 30 using conventional pattern, evaporation, and etching methodologies. In practice, sensor traces 32 and reference elements 34 are approximately five micrometers wide and between 200-2000 micrometers long (depending on the specific application). To facilitate calibration of gas sensor 10, the lengths of sensor traces 32 are approximately equal to the lengths of reference elements 34.

A plurality of gold conductor traces 42 and gold contact pads 44 may also be formed by similar deposition techniques and/or by electroplating. Conductor traces 42 provide electrical connections between contact pads 44, sensor traces 32, and reference elements 34. Contact pads 44 provide locations for wire bonding such that sensor traces 32 and reference elements 34 can be electrically connected to conductor pins 12 (see FIG. 1).

Reference elements 34 are configured such that the presence of mercury or hydrogen sulfide vapor does not measurably alter their electrical resistivity. In other words, reference elements 34 are less capable of adsorbing molecules of mercury gas and hydrogen sulfide gas than sensor traces 32, and any adsorption of such molecules by reference elements 34 occurs at a substantially lower rate than the adsorption of such molecules by sensor traces 32. Accordingly, a passivation coating 46 (see FIG. 5) is preferably deposited on the thin gold that forms reference elements 34.

Passivation coating 46 is formed by depositing a layer of material, such as molybdenum, over reference gold traces 34. If desired, other materials such as silicon dioxide or silicon nitride can be used for passivation coating 46. Passivation coating 46 functions to "protect" reference elements 34 from mercury and hydrogen sulfide vapors without otherwise affecting the resistivity of reference elements 34.

The resistivity of sensor traces 32 and reference elements 34 may be affected by temperature variations. To ensure against false detection, sensor traces 32 and reference elements 34 preferably experience the same drift in resistivity versus temperature. As such, passivation coating 46 should contribute little to the thermal conductivity of reference elements 34.

Figure 4:
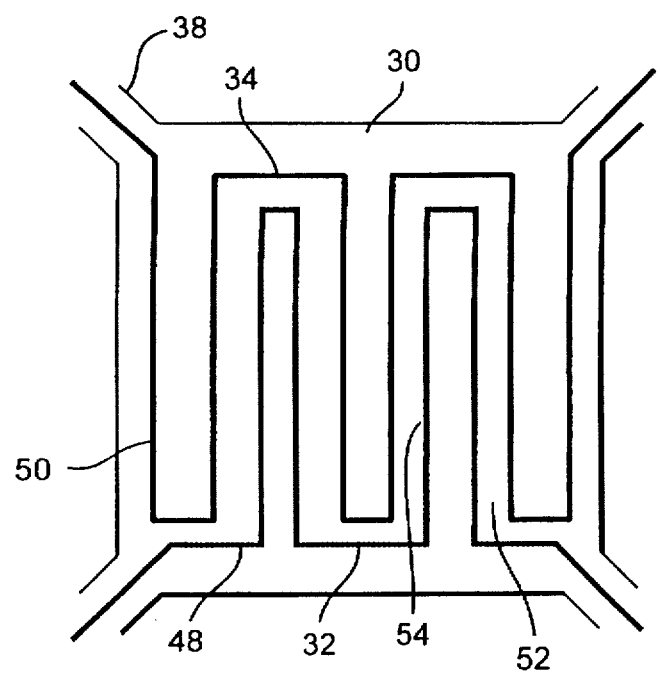
FIG. 4 is a detailed top view of a portion of the sensor chip shown in FIG. 2.

As shown in FIG. 4, each platform 30 carries one sensor trace 32 and one reference element 34. Sensor trace 32 follows a first serpentine path 48 and reference element 34 follows a second serpentine path 50. The precise shape of paths 48 and 50 may be selected according to physical packaging considerations and/or the desired electrical characteristics of sensor chip 14. For example, the serpentine configuration is desirable to achieve an adequate resistance through the gold traces while reducing the size of sensor chip 14.

First and second paths 48 and 50 are preferably shaped such that they progress in a substantially parallel spaced relationship relative to one another. In the embodiment shown in FIGS. 2 and 4, reference element 34 is shaped to define an open area 52 in the upper surface of platform 30 between continuous portions of reference element 34. A portion 54 of sensor trace 32 extends into open area 52. Alternatively, the path of reference element 34 may extend into an open area defined between continuous portions of sensor trace 32. In either case, sensor trace 32 and reference element 34 are tightly arranged next to one another on platform 30 without overlapping. The close proximity between sensor trace 32 and reference element 34 ensures that they will react similarly to local temperature changes that may affect their resistivity.

Figure 5:
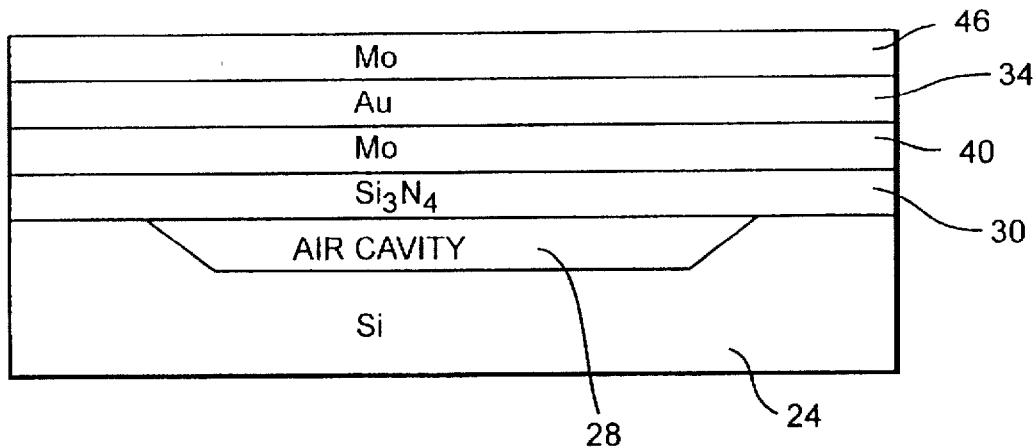
FIG. 5 is a side sectional view of a portion of the sensor chip showing layered elements utilized in the sensor chip.

FIG. 5 is a side sectional view of a portion of sensor chip 14 illustrating the various components utilized therein. The relative dimensions are exaggerated for clarity. Silicon substrate 24 forms the foundation of sensor chip 14. Cavity 28 is shown formed under a portion of silicon nitride membrane 30. Molybdenum adhesion layer 40 is deposited between membrane 30 and reference trace 34. Passivation coating 46 is shown deposited on reference trace 34. It should be appreciated that different portions of sensor chip 14 may have different cross sectional compositions than that shown in FIG. 5. For example, passivation coating 46 is not deposited on sensor traces 32 (not depicted in FIG. 5), and some portions of sensor chip 14 do not have gold traces or molybdenum adhesion layer 40 deposited thereon.

Figure 6:
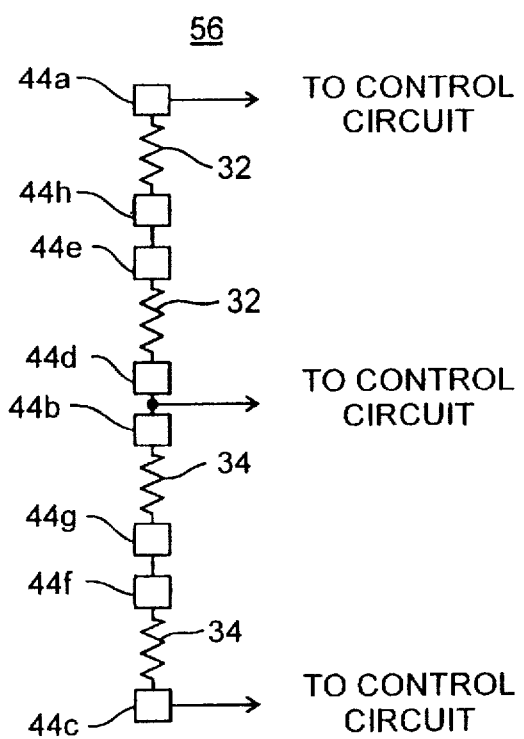
FIG. 6 is a schematic depiction of an exemplary measuring circuit configuration for the sensor chip.

FIG. 6 is a schematic depiction of an exemplary measuring circuit 56 for sensor chip 14. Contact pads 44 are indicated consistently with FIG. 2. Measuring circuit 56 is configured such that sensor traces 32 (depicted as resistors) are arranged in series with one another. Similarly, reference elements 34 (also depicted as resistors) are arranged in series with one another.

Figure 2:
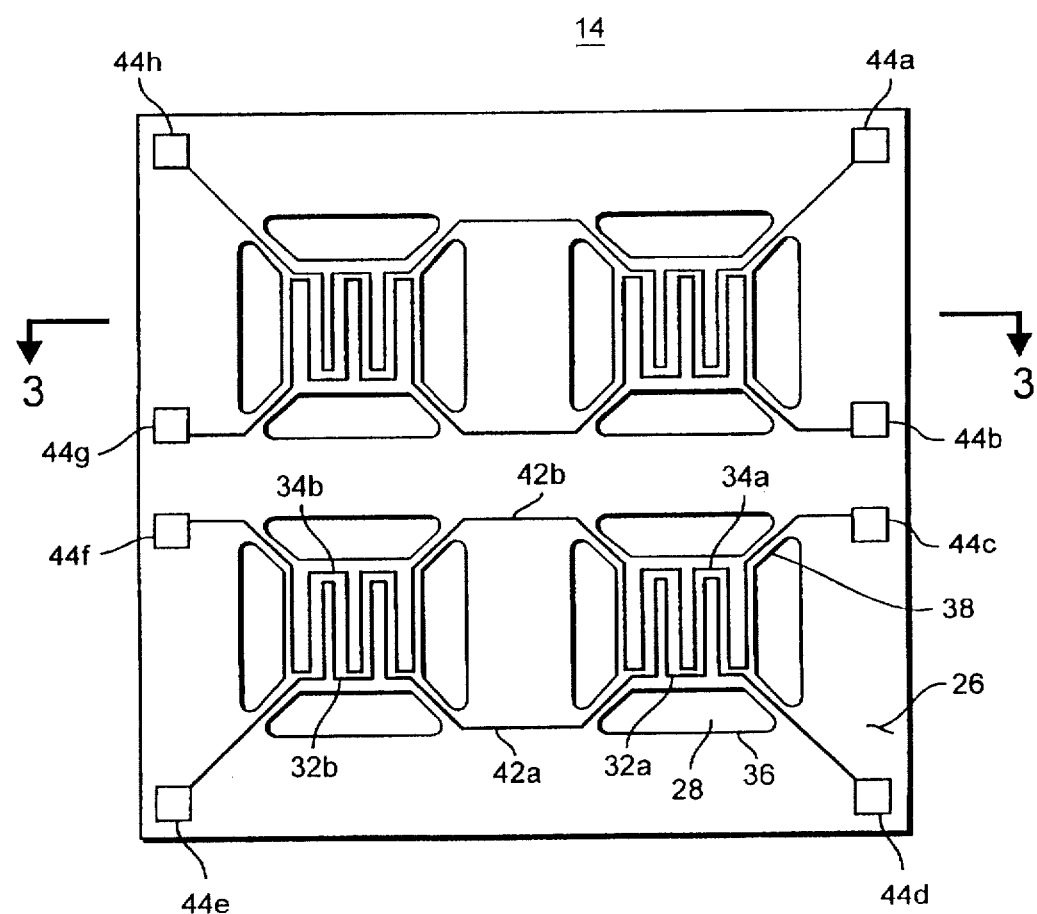
FIG. 2 is a top view of a sensor chip utilized by the gas sensor.

Each resistor in FIG. 6 represents a combination of either two sensor traces 32 or two reference elements 34. As shown in FIG. 2, a first sensor trace 32a is coupled to a second sensor trace 32b via a first continuous conductor trace 42a, and a first reference trace 34a is coupled to a second reference trace 34b via a second continuous conductor trace 42b. Nothing prevents sensor chip 14 from utilizing additional conductor traces 42 to interconnect additional sensor traces 32 and/or reference elements 34 to reduce the number of external connections and wire bonds required to implement gas sensor 10.

Referring back to FIG. 6, sensor traces 32 are connected in series with reference elements 34 by interconnecting sensor pads 44d and 44b together. Measurement points are established to enable a control circuit (not shown) to measure electrical characteristics, such as resistance, across one or more sensor traces 32 and one or more reference elements 34. When detectable amounts of mercury or hydrogen sulfide gas are present in a sample of gas, sensor traces 32 adsorb molecules of the gas while passivation coating 46 (see FIG. 5) reduces the adsorption of the gas by reference elements 34. When the resistance of sensor traces 32 changes by a predetermined amount, control circuit responds to indicate the presence of the gas. The indication threshold may be dependent upon the sensitivity of gas sensor 10, the type of gas under observation, or other application-specific parameters.

Following the detection of mercury or hydrogen sulfide gas, a regeneration process is performed to restore the detection capability of gas sensor 10. Molecules of the detected gas, which were adsorbed into the gold sensor traces 32, are liberated from sensor traces 32 when sensor traces 32 are heated to a regeneration temperature. In one preferred embodiment, sensor traces 32 are heated and regenerated when a regeneration current is passed through sensor traces 32. The regeneration current is sufficiently high to heat sensor traces 32 to a minimum regeneration temperature. Mercury molecules begin releasing from sensor traces 32 at a temperature of roughly 170° C.; hydrogen sulfide molecules begin releasing at a temperature of roughly 260° C.

Due to the small size of sensor chip 14 and the low thermal conductivity of silicon nitride membrane 26, sensor traces 32 can be regenerated quickly and efficiently. For example, a 10 mA current applied for one or two seconds can sufficiently regenerate gas sensor 10. In comparison, large ceramic sensors typically require 30–60 watts of regeneration power applied over a time period of up to 30 minutes. The low regeneration power requirement of gas sensor 10 enables it to utilize small portable batteries for regeneration. Furthermore, speedy regeneration of gas sensor 10 facilitates near real time monitoring for the presence of mercury and hydrogen sulfide gases.

Figure 7:
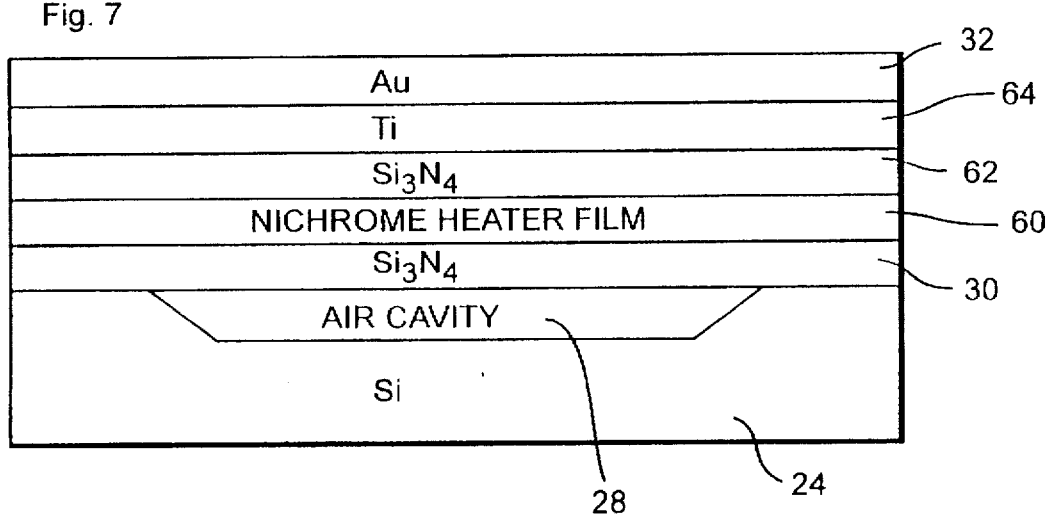
FIG. 7 is a side sectional view of a portion of an alternative sensor chip embodiment that includes an embedded heater element.
Figure 8:
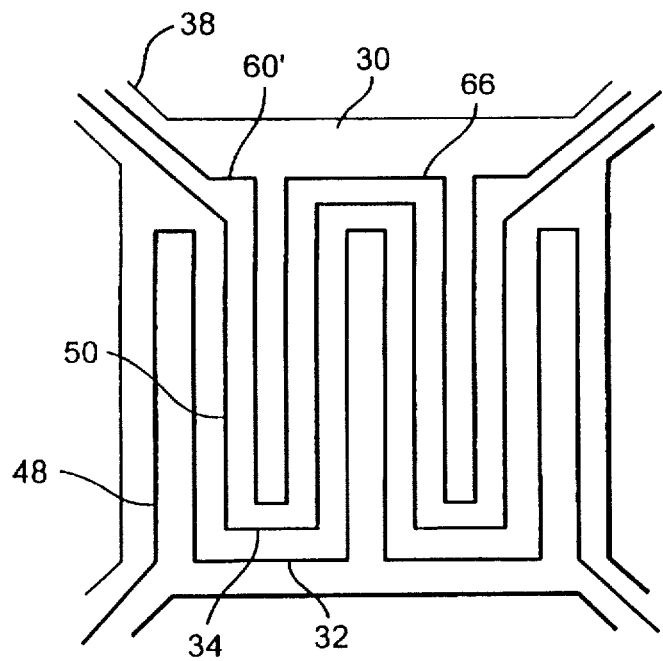
FIG. 8 is a detailed top view of a portion of an alternative sensor chip embodiment that includes an integral heater element.

Referring to FIGS. 7-8, an alternate embodiment of the present invention incorporates a heater element 60 into sensor chip 14. In the preferred embodiment, heater element 60 is formed from a material, such as a thin nichrome film, that emits heat when it conducts electricity. FIG. 7 is a side sectional view of a portion of sensor chip 14 illustrating an alternate configuration that includes an embedded heater element 60. As with FIG. 5, the relative dimensions in FIG. 7 are exaggerated for clarity and different portions of sensor chip 14 may have different cross sectional compositions than that shown.

Silicon substrate 24, air cavity 28, and nitride membrane 30 are configured as described above in connection with FIG. 5. Heater element 60 is preferably supported by and located over the upper surface of membrane 30. As shown in FIG. 8, sensor element 32, reference element 34, and heater element 60 are all located on the portion of membrane 30 that forms a platform. Heater element 60 is configured to distribute heat substantially evenly to the upper surface of membrane 30 such that sensor trace 32 is raised to the regeneration temperature when heater element 60 is activated.

As depicted in FIG. 7, heater element 60 is located between nitride membrane 30 and an upper insulating layer 62. Insulating layer may be formed from silicon nitride and it functions to protect heater element 60 and to insulate an adhesion layer 64 from direct heat. Sensor trace 32 is located above insulating layer 62 via adhesion layer 64. Adhesion layer 64 is similar to adhesion layer 40 described above in connection with FIG. 5. In particular, adhesion layer 64 is formed from a low-mobility adhesion layer, e.g., titanium, deposited on upper insulating layer 62.

Heater element 60 is embedded below sensor element 32 (and preferably below reference element 34) and is configured to apply heat evenly over membrane 30. The specific size, shape, and layout of heater element 60 may be selected to suit the needs of the particular application. For example, heater element 60 may be configured and calibrated according to the specific regeneration temperature required, the desired regeneration time, and other operational parameters.

FIG. 8 is a detailed top view of a portion of an alternative sensor chip embodiment that includes an integral heater element 60'. In contrast to the embedded heater element 60 described above, heater element 60' is surface-mounted over nitride membrane 30 along with sensor element 32 and reference element 34. As shown in FIG. 8, heater element 60' is located adjacent to sensor and reference elements 32 and 34.

In a preferred arrangement, sensor element 32 follows first path 48, reference element 34 follows second path 50, and heater element 60' follows a third path 66. First, second, and third paths 48, 50, and 66 progress in a substantially parallel spaced relationship relative to one another. Those skilled in the art will recognize that the configuration shown in FIG. 8 is merely exemplary, and that first, second, and third paths 48, 50, and 66 are not limited to any specific layout.

In summary, the present invention provides an improved sensor for detecting the presence of a specified gas within a mixture such as air. The power required to regenerate the sensor is substantially lower than the power required to regenerate an equivalent ceramic substrate sensor. In addition, the regeneration time associated with the sensor is substantially shorter than the regeneration time associated with an equivalent ceramic substrate sensor. The gas sensor can incorporate an integral heater element that provides regeneration heat evenly and uniformly. Solid state manufacturing techniques can be utilized to batch produce many individual sensors having consistent functional characteristics, which reduces calibration costs. Gold film sensor elements utilized by the sensor have electrical characteristics that are not adversely affected by the supporting substrate material or the adhesion layer material.

The above description is of a preferred embodiment of the present invention, and the invention is not limited to the specific embodiment described and illustrated. For example, nothing limits the present invention to the detection of mercury or hydrogen sulfide gases. In addition, any number of sensor traces and reference elements may be employed to suit specific needs. Furthermore, many variations and modifications will be evident to those skilled in this art, and such variations and modifications are intended to be included within the spirit and scope of the invention, as expressed in the following claims.

What is claimed is:

1. An apparatus for detecting the presence of one of a mercury gas and a hydrogen sulfide gas within a mixture, said apparatus comprising:

a substrate;

a silicon nitride membrane supported by said substrate, said membrane forming a platform having an upper surface;

a sensor element located on said upper surface, said sensor element being formed from an electrically conductive material capable of adsorbing molecules of said gas; and a reference element located on said upper surface, said reference element being configured to adsorb molecules of said gas at a substantially lower rate than said sensor element.

2. An apparatus according to claim 1, wherein said reference element is configured to be less capable of adsorbing molecules of said gas than said sensor element.

3. An apparatus according to claim 1, wherein said sensor element follows a first path, said reference element follows a second path, and said first and second paths progress in a substantially parallel spaced relationship relative to one another.

4. An apparatus according to claim 3, wherein said reference element is shaped to define an open area of said upper surface between continuous portions of said reference element, and a portion of said sensor element extends into said open area.

5. An apparatus according to claim 3, wherein said sensor element is shaped to define an open area of said upper surface between continuous portions of said sensor element, and a portion of said reference element extends into said open area.

6. An apparatus according to claim 1, wherein said substrate comprises silicon and said sensor element comprises a thin gold trace formed on said membrane.

7. An apparatus according to claim 6, further comprising a low-mobility adhesion layer deposited on said membrane, said adhesion layer facilitating adhesion of said sensor element to said membrane.

8. An apparatus according to claim 1, wherein said reference element comprises:

a thin gold trace formed on said membrane; and a passivation coating deposited on said thin gold trace.

9. An apparatus according to claim 1, wherein the length of said reference element is approximately equal to the length of said sensor element.

10. An apparatus according to claim 1, further comprising a cavity formed within said substrate under said platform.

11. An apparatus according to claim 1, wherein the electrical resistivity of said sensor element changes when molecules of said gas are adsorbed by said sensor element.

12. An apparatus for detecting the presence of one of a mercury gas and a hydrogen sulfide gas within a mixture, said apparatus comprising:

a substrate;

a silicon nitride membrane supported by said substrate, said membrane forming a platform having an upper surface;

a low-mobility adhesion layer deposited on said membrane, said adhesion layer facilitating adhesion of gold to said membrane; and a gold sensor trace located on said upper surface and deposited on said adhesion layer, said sensor trace being capable of adsorbing molecules of said gas.

13. An apparatus according to claim 12, wherein said adhesion layer is selected from the group consisting of molybdenum, titanium, tungsten, and titanium-tungsten alloy.

14. An apparatus according to claim 12, further comprising a reference element located on said upper surface, said reference element being configured to adsorb molecules of said gas at a substantially lower rate than said sensor trace.

15. An apparatus according to claim 14, wherein said sensor trace follows a first path, said reference element follows a second path, and said first and second paths progress in a substantially parallel spaced relationship relative to one another.

16. An apparatus according to claim 14, wherein said reference element is shaped to define an open area of said upper surface between continuous portions of said reference element, and a portion of said sensor trace extends into said open area.

17. An apparatus according to claim 14, wherein the length of said reference element is approximately equal to the length of said sensor trace.

18. An apparatus according to claim 14, wherein said reference element comprises:

a gold reference trace deposited on said adhesion layer; and a passivation coating deposited on said reference trace.

19. An apparatus according to claim 12, wherein the electrical resistivity of said sensor trace changes when molecules of said gas are adsorbed by said sensor trace.

20. An apparatus according to claim 12, wherein molecules of said gas are liberated from said sensor trace when said sensor trace is heated to a regeneration temperature.

21. An apparatus according to claim 12, wherein molecules of said gas are liberated from said sensor trace when a regeneration current is passed through said sensor trace.

22. An apparatus for detecting the presence of one of a mercury gas and a hydrogen sulfide gas within a mixture, said apparatus comprising:

a substrate; and a silicon nitride membrane suspended above said substrate, said membrane forming a plurality of platforms;

a plurality of cavities formed within said substrate, said cavities being formed under said platforms;

a plurality of gold sensor traces located on said membrane, each of said sensor traces being capable of adsorbing molecules of said gas; and a plurality of reference traces located on said membrane, each of said reference traces being configured to adsorb molecules of said gas at a substantially lower rate than said sensor traces; wherein each of said platforms carries one of said sensor traces and one of said reference traces.

23. An apparatus according to claim 22, wherein:

a first sensor trace is coupled to a second sensor trace via a first continuous conductor trace; and a first reference trace is coupled to a second reference trace via a second continuous conductor trace.

24. An apparatus according to claim 22, wherein the electrical resistivity of said sensor traces changes when molecules of said gas are adsorbed by said sensor traces.

25. An apparatus according to claim 22, further comprising a low-mobility adhesion layer deposited on said membrane, said adhesion layer facilitating adhesion of said sensor traces to said membrane.

26. An apparatus for detecting the presence of one of a mercury gas and a hydrogen sulfide gas within a mixture, said apparatus comprising:

a substrate;

a membrane supported by said substrate, said membrane forming a platform having an upper surface;

a sensor element located on said upper surface, said sensor element being formed from an electrically conductive material capable of adsorbing molecules of said gas; and a container configured to accommodate said substrate, said container having a cylindrically shaped wall and a top cover attached to said wall.

27. An apparatus according to claim 26, wherein said container includes an inlet hole formed in said top cover for introduction of said mixture.

28. An apparatus according to claim 27, wherein said inlet hole is sized to regulate flow of said mixture into said container.

29. An apparatus for detecting the presence of one of a mercury gas and a hydrogen sulfide gas within a mixture, said apparatus comprising:

a substrate;

a membrane supported by said substrate, said membrane forming a platform having an upper surface;

a sensor element supported by and located over said upper surface, said sensor element being formed from an electrically conductive material capable of adsorbing molecules of said gas;

a reference element supported by and located over said upper surface, said reference element being configured to adsorb molecules of said gas at a substantially lower rate than said sensor element; and a heater element supported by and located over said upper surface, said heater element being configured to distribute heat substantially evenly to said upper surface such that said sensor element is raised to a regeneration temperature when said heater element is activated.

30. An apparatus according to claim 29, wherein said sensor element follows a first path, said reference element follows a second path, said heater element follows a third path, and said first, second, and third paths progress in a substantially parallel spaced relationship relative to one another.

31. An apparatus according to claim 30, wherein said substrate comprises silicon, said membrane comprises silicon nitride, and said heater element comprises a nichrome film formed on said membrane.

32. An apparatus according to claim 32, wherein said heater element is located between said membrane and said sensor element.

33. An apparatus according to claim 32, wherein:

said heater element is located between said membrane and an upper insulating layer; and said sensor element is located above said upper insulating layer.

34. An apparatus according to claim 32, wherein said membrane and said upper insulating layer are comprised of silicon nitride.

35. An apparatus according to claim 34, wherein:

said sensor element is formed from a thin gold film; and said apparatus further comprises a low-mobility adhesion layer deposited on said upper insulating layer, said adhesion layer facilitating adhesion of said sensor element to said upper insulating layer.

* * * * *

UNITED STATES PATENT AND TRADEMARK OFFICE
CERTIFICATE OF CORRECTION

PATENT NO.   : 5,759,493
DATED        : 2 June 1998
INVENTOR(S)  : Walfred R. Raisanen It is certified that error appears in the above-indentified patent and that said Letters Patent is hereby corrected as shown below:

In the Column 10, Line 27, after "a" insert --silicon nitride--.

In the Column 10, Line 47, after "a" insert --silicon nitride--.

In the Column 11, Lines 2-3, delete ", said membrane comprises silicon nitride,".

In the Column 11, Line 5, change "32" to --29--.

In the Column 12, Line 2, delete "membrane and said".

In the Column 12, Line 2, change "are" to --is--.

Signed and Sealed this

First Day of September, 1998

Attest:

BRUCE LEHMAN

*Attesting Officer*                         *Commissioner of Patents and Trademarks*